United States Patent [19]

Taylor

[11] Patent Number: 5,760,414
[45] Date of Patent: Jun. 2, 1998

[54] WEB OF RECORD MEMBERS AND METHOD OF AND APPARATUS FOR MAKING SAME AND SYSTEM FOR DETECTING INDICIA

[75] Inventor: John W. Taylor, Springboro, Ohio

[73] Assignee: Monarch Marking Systems, Inc., Dayton, Ohio

[21] Appl. No.: 574,703

[22] Filed: Dec. 19, 1995

[51] Int. Cl.$^6$ .................................................. G01N 21/86
[52] U.S. Cl. ................. 250/559.42; 250/559.45; 356/430
[58] Field of Search ................. 250/559.42, 559.43, 250/559.45, 559.46; 356/237, 430

[56] References Cited

U.S. PATENT DOCUMENTS

| | | | |
|---|---|---|---|
| 3,340,400 | 9/1967 | Quittner | 250/219 |
| 3,800,701 | 4/1974 | Martin | 101/288 |
| 3,812,348 | 5/1974 | Lippke | 250/561 |
| 3,835,332 | 9/1974 | Bridges | 250/563 |
| 4,002,279 | 1/1977 | Klein | 226/2 |
| 4,274,661 | 6/1981 | Jenkins | 283/21 |
| 5,243,408 | 9/1993 | Whitman, III | 356/430 |

*Primary Examiner*—Edward P. Westin
*Assistant Examiner*—Kevin Pyo
*Attorney, Agent, or Firm*—Joseph J. Grass

[57] ABSTRACT

There is disclosed a web of record members of the composite label web, tag and linerless types with cracks or fissures through the webs so that the position of the web can be detected by an optical detector. Apparatus can be used to convert the web into more usable form which includes for provision of optically detectable cracks or fissures in the web. These cracks are made by crushing the web locally between one or more crushing cutters and a back-up roll which cooperates with zero clearance. The method and apparatus can produce a reliably detectable web at low cost. The optical detector includes a source of light and a bicell detector between which the web with the cracks or fissures passes. The bicell detector produces a first output signal representing the amount of light impinging on a first portion of the detector and a second output signal representing the amount of light impinging on a second portion of the detector. A difference circuit is coupled to the bicell detector to provide a signal representing the difference between the first and second output signals of the bicell detector. From this difference signal the leading and trailing edges of a crack or fissure can be detected.

20 Claims, 6 Drawing Sheets

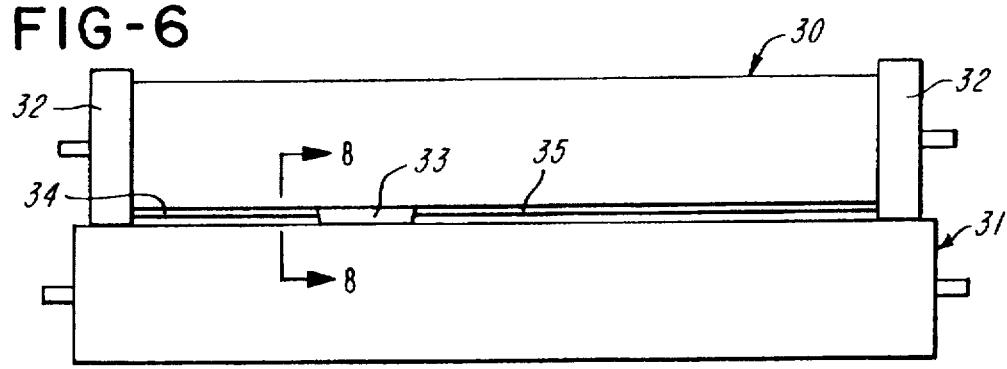
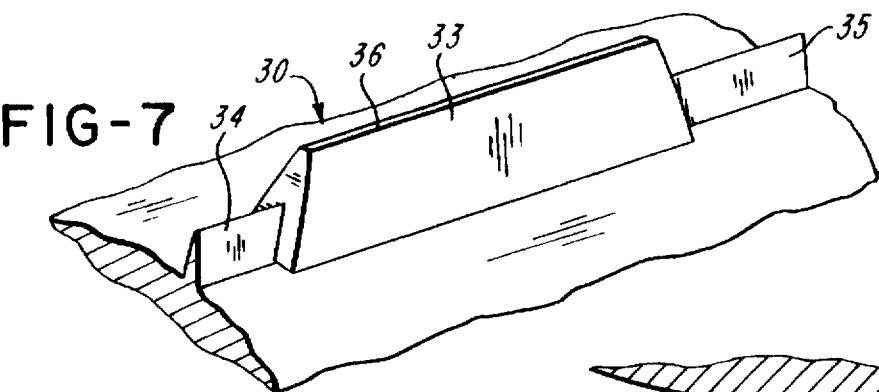
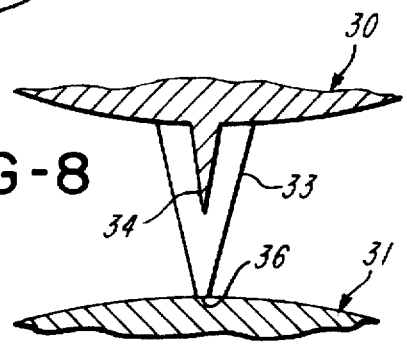
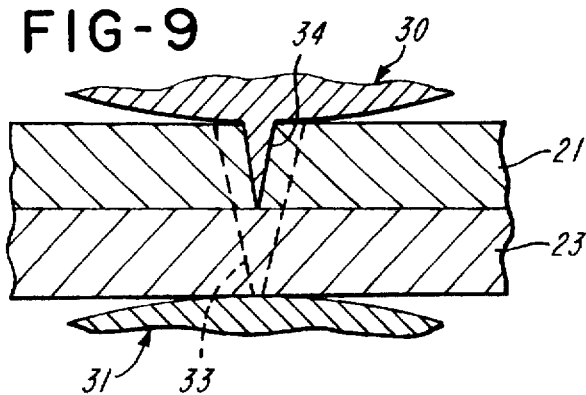
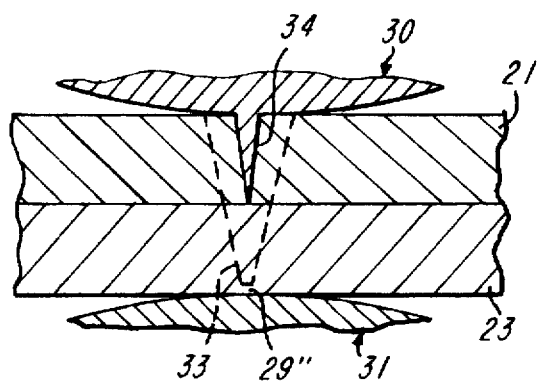

WEB OF RECORD MEMBERS AND METHOD OF AND APPARATUS FOR MAKING SAME AND SYSTEM FOR DETECTING INDICIA

BACKGROUND OF THE INVENTION

1. Field of the Invention

This invention relates to the art of webs of record members and to methods of and apparatus for making same.

2. Brief Description of the Prior Art

U.S. Pat. No. 4,002,279 to Klein discloses that notches in webs can be used to control registration in a printer. A major disadvantage of this approach resides in the need to remove and discard small plugs of material, known as "chad" during manufacture of such webs. In addition, when the web is a composite pressure sensitive label web, adhesive can to adhere to punches and dies, further complicating the manufacturing process.

U.S. Pat. No. 3,800,701 to Martin shows lateral feed slits or cuts in the carrier web of a composite label web which can coincide or be aligned with butt cuts in the label material. A "butt cut" is an essentially complete line of severing through the label material web but not into the carrier web. However, such feed slits that understandably are made with knives sharp enough to make good feed slits but these feed slits do not produce a through crack in the carrier web, or crush the carrier web to the extent, to allow for reliable detection of light therethrough.

U.S. Pat. No. 4,274,661 to Jenkins shows that feed slits can be made in the carrier web and these feed slits allow one or more flaps to be displaced from the plane of the carrier web.

SUMMARY OF THE INVENTION

The invention pertains to a web of record members with an improved arrangement by which the position of the web can be optically detected for registration purposes.

More specifically, it is a feature of the invention to provide an improved web of record members that is easy-to-manufacture, is low in cost, does not remove chad from or displace a portion of the web from the plane of the web, and which can be used to detect reliably the position of the web for registration purposes.

In accordance with specific embodiments of the invention, a web of record members is provided with a series of optically detectable crushed areas and preferably having cracks or fissures disposed at equally longitudinally spaced intervals. It is preferred that the cracks be made by crushing. In one embodiment of the invention, the crushing produces lateral cracks or fissures occurring in the record material web. These crushed areas or cracks or fissures allow enough light to pass through the web to enable reliable detection.

It is preferred that when applying the invention to a composite label web the cracks in the carrier web be made at the butt cuts. In this way an integral butt cutter and crushing element can simultaneously make a butt cut and a crushed area. There is resultant exact registration between the butt cuts and the crushed areas or cracks so that there is exact registration between the labels and the crushed areas or cracks.

The invention is also applicable to webs of tag stock and to linerless pressure sensitive label webs. In such uses the tool comprises a roll with one or more crushing elements and a cooperable back-up roll. The crush element makes a crushed area and preferably a crack or fissure in the web each time it cooperates with the back-up roll so that registration crushed areas or preferably cracks are formed at regular, equally spaced apart intervals. The crush area or cracks allow enough light to pass through the web so that the web can be used for registration purposes.

It is preferred to provide a one-piece tool for making the butt cut and for crushing the carrier web to provide each detectable crushed area or crack.

It is preferred to provide a one-piece rotatory tool for crushing the carrier web to provide each crushed area or crack.

It is preferred to provide an apparatus including a pair of cooperating rolls between which the web of record members can be passed. One of these rolls has a crushing element which crushes the web locally at equally longitudinally spaced intervals to make optically detectable crushed areas or cracks in the web.

In order to detect a crack or fissure forming an optically detectable indicium, a source of light and an optical detector are employed. In the illustrated embodiment, the optical detector is positioned relative to the source of light to detect light impinging on the detector and the detector is spaced from the source of light to allow the web of record members with the crack or fissure to pass therebetween. The optical detector generates a first output signal representing an amount of light impinging on a first portion of the detector and a second output signal presenting an amount of light impinging on a second portion of the optical detector. A difference circuit is responsive to the first and second output signals to produce a signal that represents the difference therebetween. The difference signal is compared to a reference signal in order to identify an edge of the crack or fissure. The leading and trailing edges of a crack or fissure are thus detectable for accurate registration of the record members with respect to a printhead for printing thereon. There is a predetermined relationship between the crack or fissure and the related label or tag. The label or tag is a top of form position when the printing cycle begins and the top of form position is determined by detection of a crack or fissure (indicium) by the detector at the end of the next previous printing cycle.

BRIEF DESCRIPTION OF THE DRAWINGS

FIG. 6 is a side elevational view of a cutting and crushing roll and a cooperating back-up roll according to one embodiment of the invention;

FIG. 7 is an enlarged fragmentary perspective view of the cutting and crushing roll shown in FIG. 6;

FIG. 8 is a fragmentary sectional view taken generally alone line 8—8 of FIG. 6 showing the crushing element in elevation and the butt cutter in section, absent a composite label web;

FIG. 9 is a view like FIG. 8 but in addition showing a composite label web showing the impression made by the crushing element in broken lines;

FIG. 10 is a view similar to FIG. 9 but showing the result of the spacing the crushing element slightly from the back-up roll;

DETAILED DESCRIPTION OF THE PREFERRED EMBODIMENTS

Figure 1:
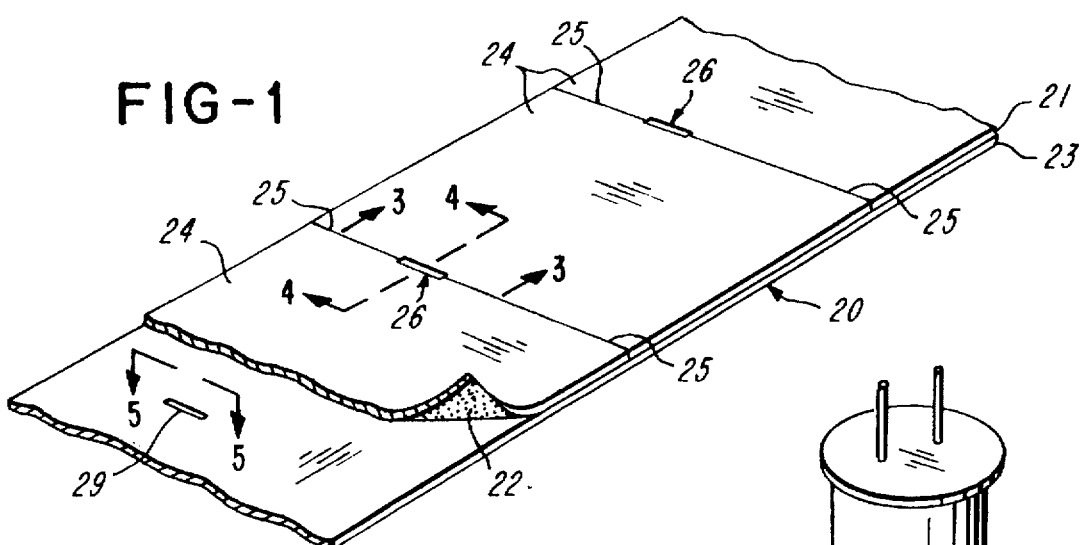
FIG. 1 is a perspective view of a composite web of labels embodying the invention.

With reference to FIG. 1, there is shown a composite label web 20 comprised of a longitudinally extending web of label material web 21 having a coating of pressure sensitive adhesive 22 on its underside. The label material web 21 preferably has a printable upper surface. The label material web 21 is releasably adhered by the adhesive 22 to a release coated longitudinally extending carrier web or liner 23.

Figure 2:
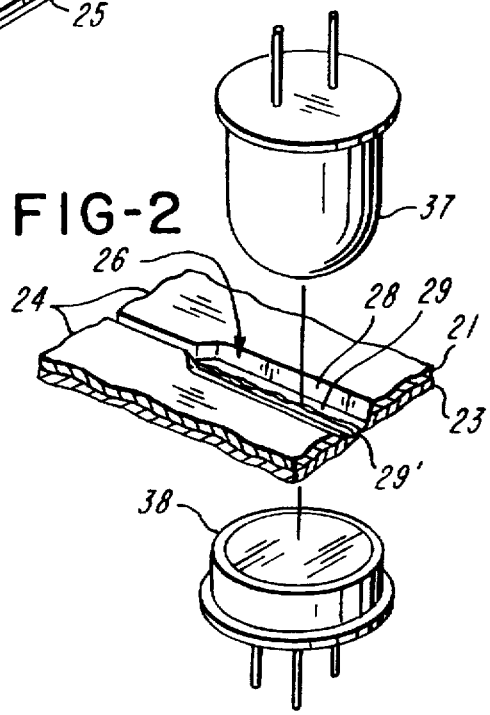
FIG. 2 is a fragmentary perspective view of the web shown in FIG. 1 together with a light source and an optical detector or sensor.
Figure 5:
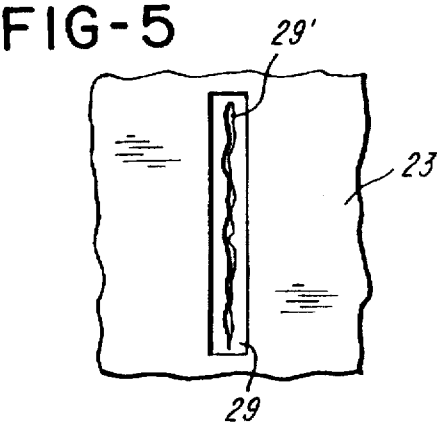
FIG. 5 is an enlarged fragmentary top plan taken generally along line 5—5 of FIG. 1.
Figure 3:
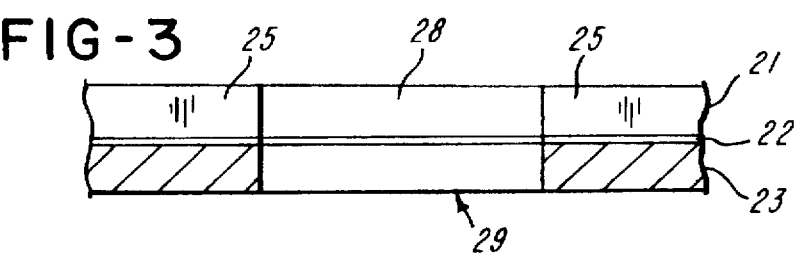
FIG. 3 is a sectional view taken generally along the butt cut in FIG. 1.
Figure 4:
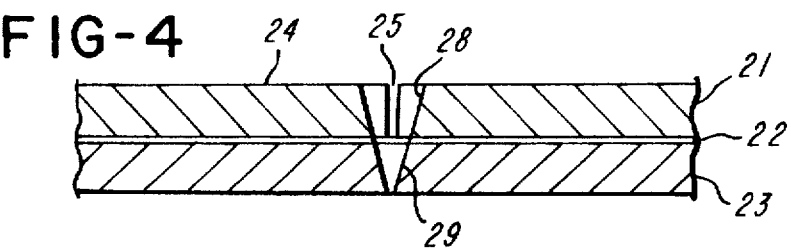
FIG. 4 is a sectional view taken generally along line 4—4 of FIG. 1.

The label material web 21 is separated into a series of labels 24 by completely severing or cutting at equally longitudinally spaced laterally extending lines 25. The labels 24 are provided by preferably simultaneously butt cutting the label material web 21 and by crushing localized areas along the laterally extending lines 25. The resultant butt cuts are indicated at 25 and the resultant optically detectable crushed areas are generally indicated at 26. As shown, each crushed area 26 is comprised of a crush area 28 in the label material web 21 and by a crushed area 29 with a crack or fissure 29' in the carrier web 23. The label material web 21 and the carrier web 23 are comprised of paper having paper fibers. As crushing occurs, the fibers of the paper are crushed, and cracks or fissures 29' result. The cracks 29' go through the carrier web 23 as best shown in FIG. 2. The cracks 29' are shown to be irregular.

FIG. 6 shows a roll generally indicated at 30 and a back-up roll generally indicated at 31. Annular bearers 32 at each end of the roll 30 bear against the surface of the back-up roll 31 which is annular in section. The bearers 32 maintain the spacing between the rolls 30 and 31. As shown in FIGS. 6 and 7, a crushing element 33 is disposed on the surface of the roll 30 in alignment with butt cutting knives or butt cutters 34 and 35. The crushing element 33 and the butt cutters 34 and 35 and the roll 30 are of one-piece unitary construction. The number of crushing elements 33 and butt cutters 34 and 35 about the periphery of the roll 30 is dependent on the diameter of the roll 30 and the length of the labels 24. The butt cutters 34 and 35 are relatively sharp in that they are required to cut through the label material web 21 but not into the carrier web 23. The crushing element 33 must not only crush through the label material web 21 but must also crush the carrier web 23 locally. It is preferred that there be zero clearance between the blade-like crushing element 33 and the surface of the roll 31 as best shown in FIG. 8. Also the crushing element 33 is blunt and preferably has a flat edge surface 36. This arrangement causes the carrier web 23 to fracture at the place where the crushing element 33 cooperates with the back-up roll 31. The carrier web 23 that is in the path between the flat edge surface 36 and the back-up roll 31 as shown in FIG. 9 is cammed or pushed aside thereby pushing aside the label material web 21 adjacent the crushing elements 33 (33') and thinning out the carrier web 23. There can still exist some fibers between the cooperating edge surface 35 and the back-up roll 31 but such fibers are crushed or smashed to the extent that cracks or fissures 29' are formed which are large enough to let light pass through. Therefore, these cracks enable the position of the composite web 20 to be reliable detected in a utilization device such as a printer or the like.

FIG. 2 illustrates a light source 37, preferably an infra-red light source, and an infra-red optical detector or sensor 38. Light passing through the crushed area 26 and in particular through the crack 29' in the carrier web 23 is detected by the sensor 38.

FIG. 10 shows an embodiment identical to the embodiment of FIGS. 1 through 9 except that crushing element 33 terminates slightly short of the surface of the roll 31 by, for example. 0.0001 inch. This results in a crushed area 29' of the carrier web 23 between the flat edge surface 36' and the roll 31. The crushed area 29' is wide enough and is crushed and thinned out to such an extent that the light from the source 37 is capable of being reliably detected therethrough by the detector 38.

Figure 11:
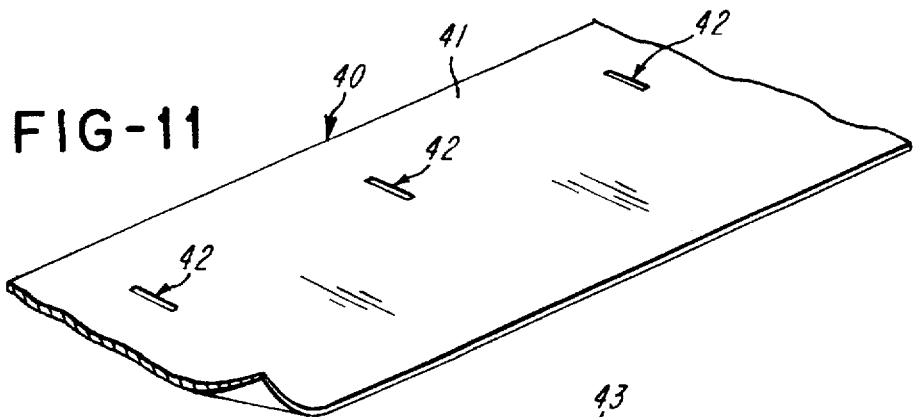
FIG. 11 is a fragmentary perspective view of a web of printable tag stock embodying the invention.
Figure 15:
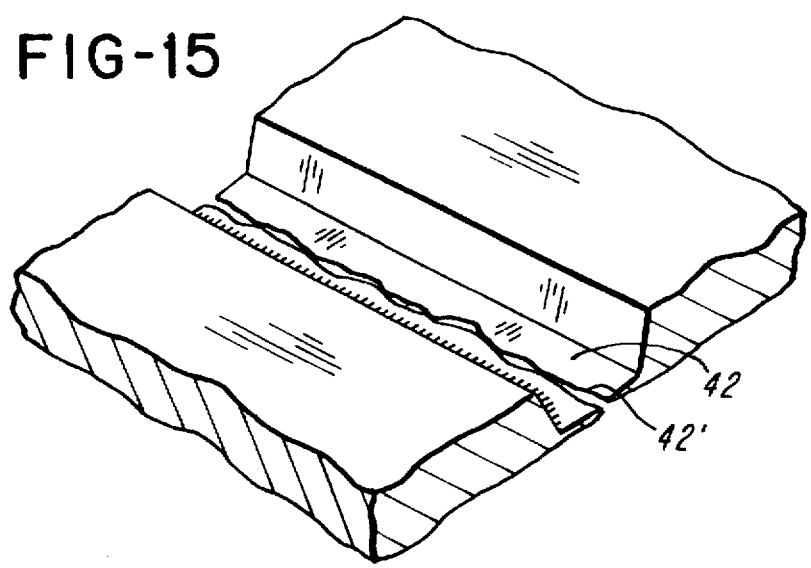
FIG. 15 is a fragmentary perspective view depicting the crushed areas of each of FIGS. 11 through 14.

FIG. 11 illustrates the invention used in connection with a tag web 40 comprised of a printable web of web stock 41. The web 41 is provided with equally longitudinally spaced transversely extending crushed areas generally indicated at 42 preferably resulting in cracks or fissures 42'. The cracks 42' go through the web 40 and area irregular as shown in FIG. 15. The crushed areas 42 allow light to pass through as in the embodiment of FIGS. 1 through 9. The web 40 can be separated into individual tags for example by a cutter as disclosed in co-owned U.S. Pat. No. 4,693,151 to Goubeau.

Figure 12:
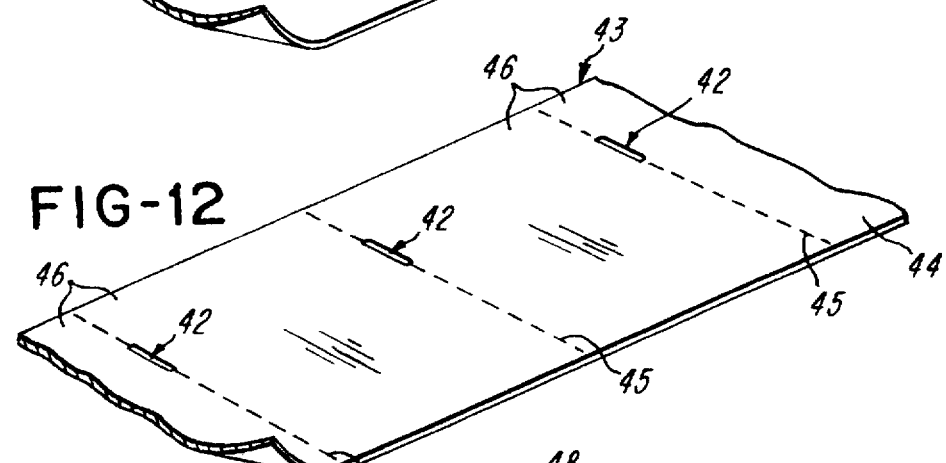
FIG. 12 is a fragmentary perspective view of a web of tag stock as shown in FIG. 11, but having lateral perforation cuts aligned with the crushed areas.

The embodiment of FIG. 12 has the same crushed areas 42 resulting preferably in cracks or fissures 42' in a web 43 of tag stock 44, but additionally there are perforation cuts 45 aligned with the crushed areas 42. The perforation cuts 45 define tags 46. The perforation cuts 45 help in separating the tags 46 from the remainder of the web 43.

Figure 13:
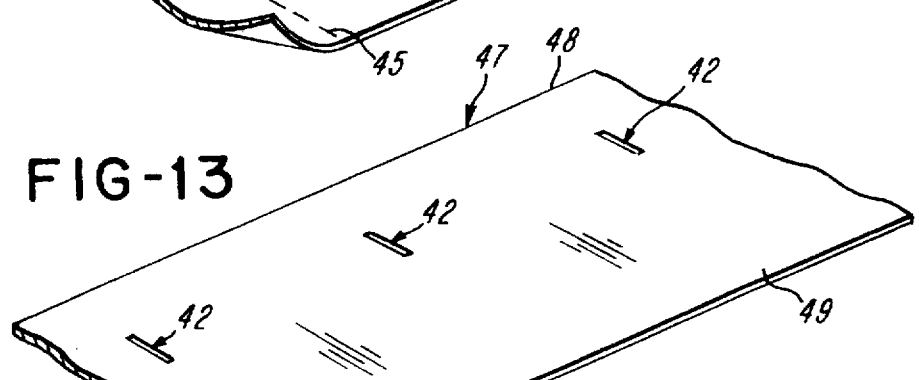
FIG. 13 is a fragmentary perspective view of a web of linerless pressure sensitive labels embodying the invention.

With reference to FIG. 13 these is shown a label web 47 comprised of a linerless pressure sensitive label material web 48. The web has a printable upper surface 49 having a release coating. The underside of the web 48 has a coating of pressure sensitive adhesive 50. Cracked areas 42 enables feed registration of the web 47 to be maintained.

Figure 16:
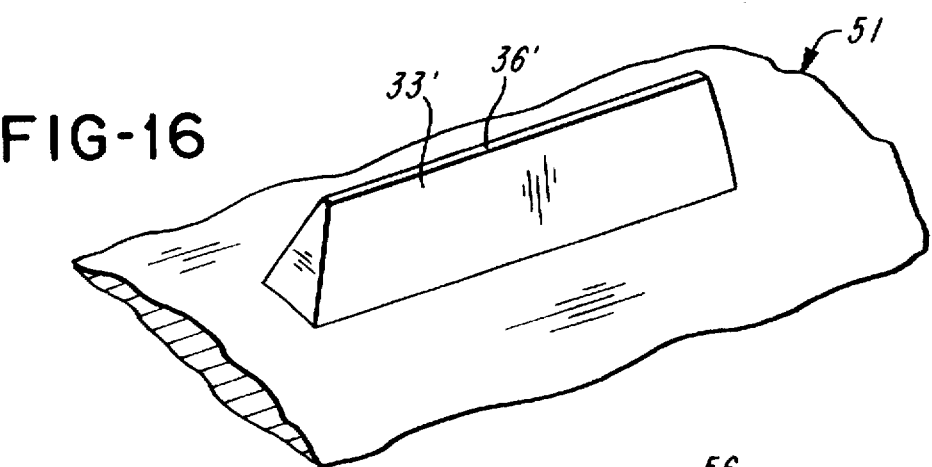
FIG. 16 is an enlarged fragmentary perspective view of a roll showing the crushing element for making the crush cuts in the webs of the embodiments of FIGS. 11 and 13.

It is to be noted that the crushing roll 51 shown in FIG. 16 has one or more peripherally spaced crushing elements 33' like the crushing element 33. The roll 51 can make the webs 40 and 47 shown in FIGS. 11 and 13, respectively.

Figure 14:
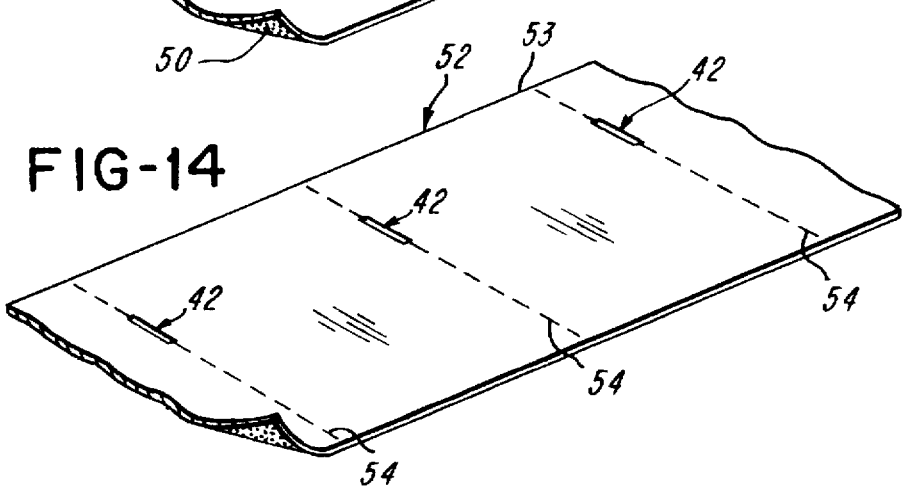
FIG. 14 is a fragmentary perspective view of a web of linerless pressure sensitive label material as shown in FIG. 13, but having lateral perforation cuts aligned with the crushed areas.
Figure 17:
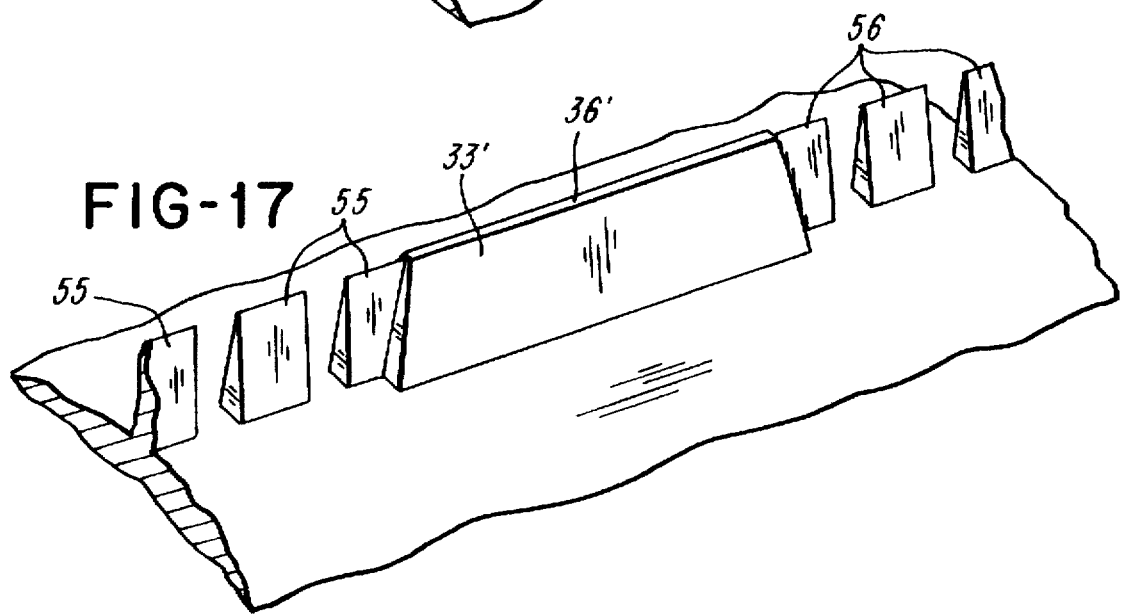
FIG. 17 is a fragmentary perspective view of a roll showing the crushing element and perforation cutter for making the crush areas and the perforation cuts in the webs of the embodiments of FIGS. 12 and 14.

A label web 52 (FIG. 14) comprised of a linerless pressure sensitive label material web 53 is like that shown and described with respect to FIG. 13 except that in the embodiment of FIG. 14 perforation cuts 54 are provided in alignment with the crushed areas 42. The crushed areas 42 and resulting cracks or fissures 42' are made by a crushing element 33' shown in FIG. 17. The crushing element 33' is disposed between and in alignment with perforating knives 55 and 56.

The webs 21, 23, 40, 43, 47 and 52 is preferably comprised of paper.

The flat edge surface 36 (36') is preferably in the range of about 0.010 inch wide to about 0.020 inch wide and most preferably about 0.015 inch wide. A flat edge surface 36 (36') somewhat of in excess of 0.020 inch is also effective however, but as the width of the flat edge surface increases there is increased wear on the crushing element 33 (33'). In the event the flat edge surface is too wide, there would be a tendency merely to compact an area of the web instead of thinning out the web adequately to produce an optically detectable crushed area. By way of example, not limitation, the length of the flat edge surface 36 (36') is about 0.30 inch.

In order to detect a crack or fissure 29' in the composite label web 20, the light source 37 is positioned on one side 54 of the web 20 whereas the optical detector 38 is positioned on an opposite side 56 of the web 20. As discussed above, the light source 37 is preferably an infrared light source having preferably a nominal wave length of 880 nm. The optical detector 38 is preferably a bicell detector having a first active or sensitive portion 60 and a second active or sensitive portion 62 separated by a predetermined distance or gap 64. The area of each of the first and second active portions 60, 62 of the optical detector 38 can preferably be on the order of 0.180×0.020 sq. inches; wherein the predetermined spacing 64 between the active portions 60 and 62 of the optical detector 38 can be on the order of preferably 0.0008 inches. Preferably, the light source 37 is positioned directly above the gap 64 and so as to be centered between the active portions 60 and 62 of the optical detector 38.

As the composite label web 20 is moved in the direction of the arrow 66 between the light source 37 and the optical detector 38, the highest percentage of light from the source 37 impinges first upon an area 68 of the active detector portion 60 above which the crack 29' is positioned. As the composite label web 20 moves the crack 29' farther in the direction of the arrow 66, the highest percentage area 68 of illumination moves so that it is centered above the gap 64 between the active detector portions 60 and 62 when the crack 29' is centered thereabove. As the composite label web 20 continues its movement in the direction of the arrow 66, so that the crack 29' is above the active portion 62 of the optical detector 38, the highest percentage area of illumination 66 occurs on the active detector portion 62 when the crack 29' is positioned thereabove. Because a greater amount of light will impinge on one of the active detector portions 60 or 62 when the crack 29' is positioned directly thereabove, a potential difference will be developed between the two active portions 60 and 62. This potential difference is detected by a difference circuit 70, the output of which is illustrated in FIG. 19.

Figure 19:
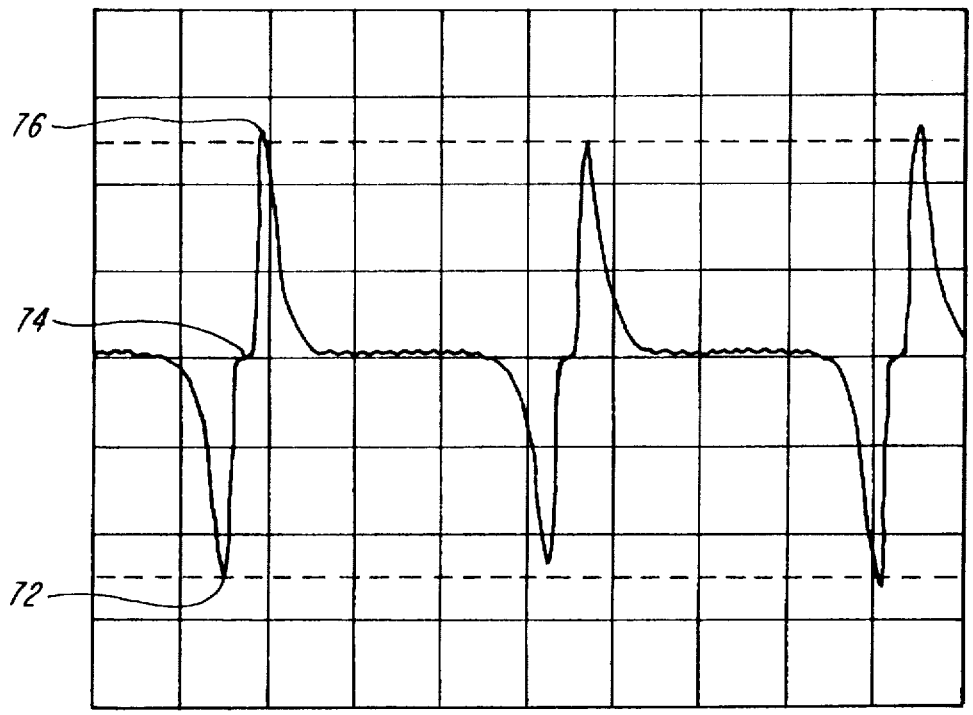
FIG. 19 is a waveform illustrating the output of a difference circuit of the optical detector.

As can be seen from FIG. 19, when the crack or fissure 29' in the composite label web 20 is centered above one of the active elements such as the element 60, the output of the difference circuit 70 peaks in the negative direction at a point 72. As the crack or fissure 29' is centered above the gap 64 between the active detector portions 60 and 62 of the optical detector 38, the difference between the amount of light detected by each of the active detector portions 60 and 62 is approximately equal so that the output of the difference circuit 70 goes to zero or a null point 74. Thereafter, as the crack or fissure 29' becomes centered above the other active portion 62 of the optical detector 38, a peak 76 in the positive direction is produced in the signal output from the circuit 70.

Figure 18:
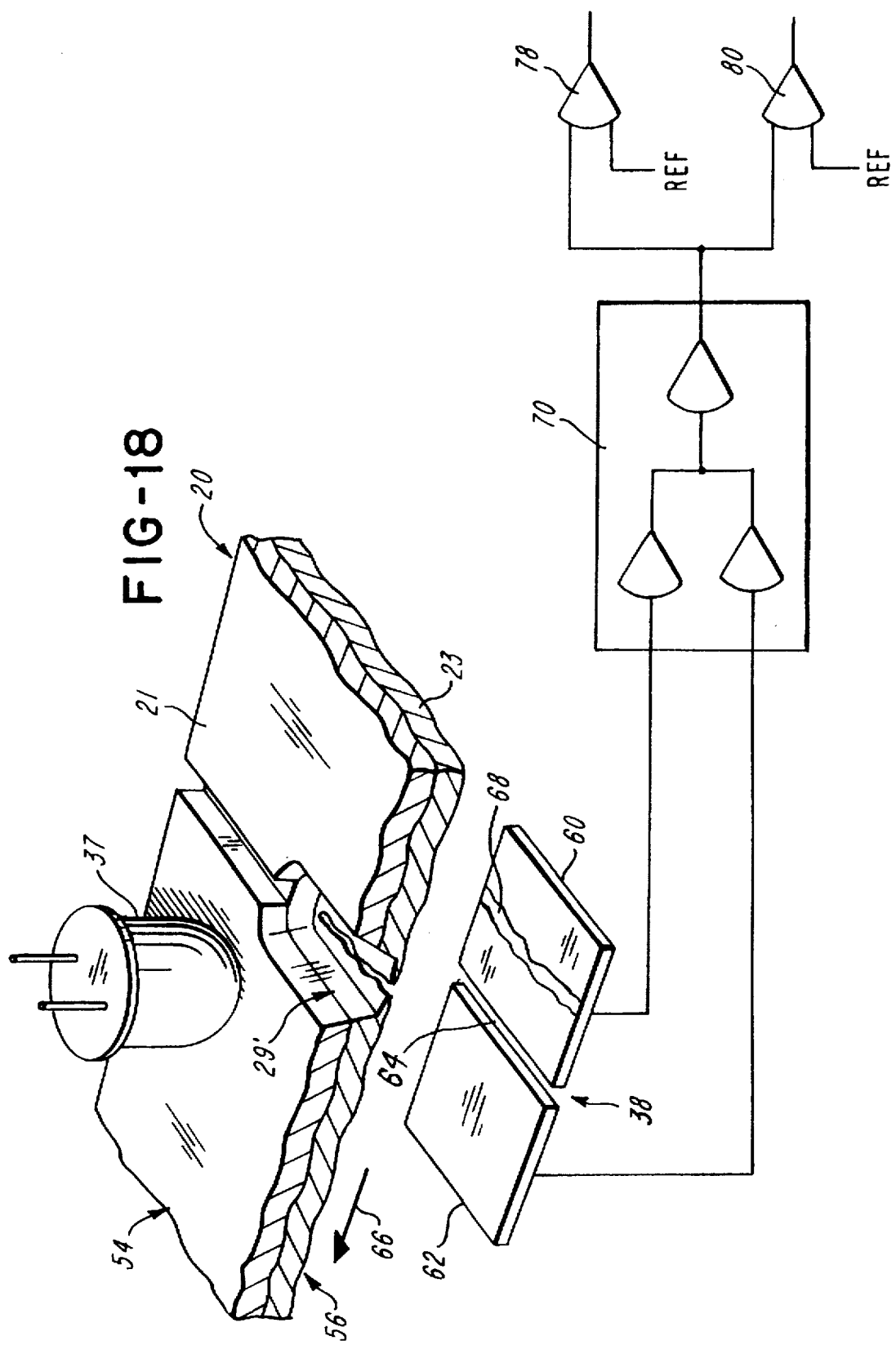
FIG. 18 is a perspective view of a composite web of labels in accordance with the present invention in relation to a light source and optical detector, a portion of which is shown in block diagram form.

The signal output from the difference circuit 70 may be applied to a comparator circuit formed of a first comparator 78 and a second comparator 80 as shown in FIG. 18. The comparator 78 compares the difference signal output from the circuit 70 to a first reference signal and produces an output when the difference signal is less than the first reference signal. Similarly, the comparator 80 compares the difference signal output from the circuit 70 to a second reference signal and produces an output when the difference signal is greater than the second reference signal. An output from the respective comparators 78 and 80 represents a respective edge of the crack or fissure 29'. The output from the comparators 78 and 80 can represent respectively either the leading edge or the trailing edge of the crack or fissure 29' depending on the direction of movement of the composite label web 20 with respect to the active detector portions 60 and 62 of the optical detector 38.

Figure 20:
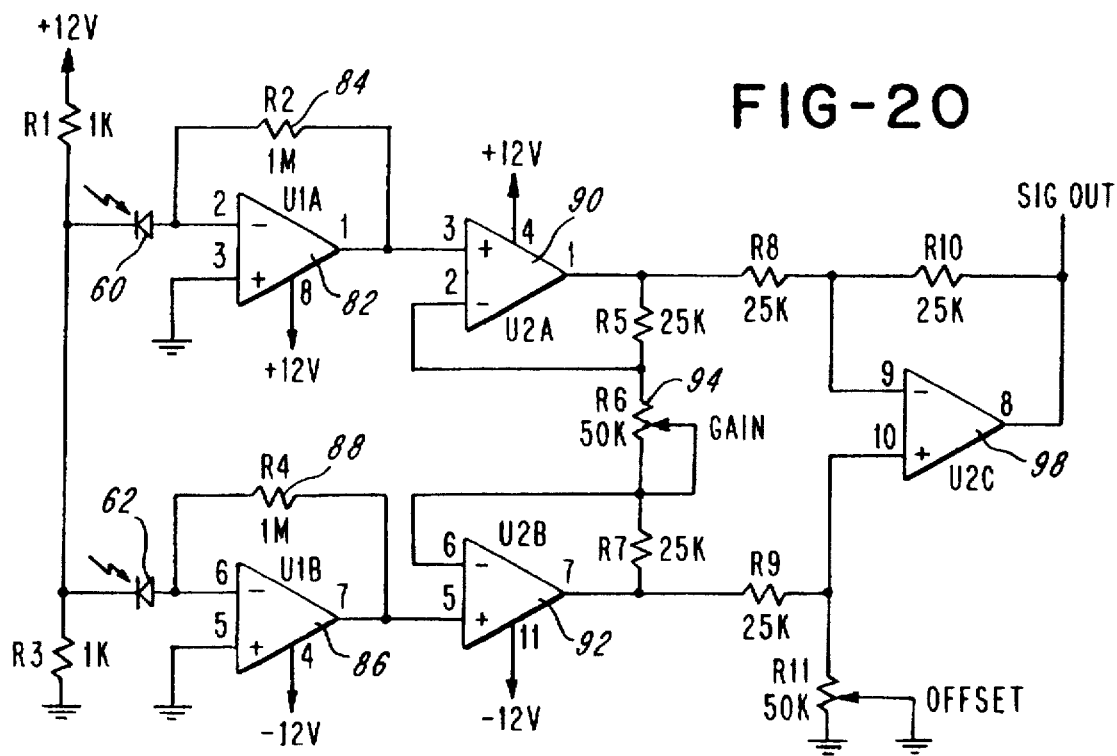
FIG. 20 is a detailed schematic diagram of the difference circuit illustrated in FIG. 18.

Details of the difference circuit 70 are illustrated in FIG. 20. As shown therein, the active portion 60 and the active portion 62 are depicted as photodetector elements in the form of photodiodes. The photodetector elements 60 and 62 are operated in a photoconductive mode in which an external reverse bias is applied thereto by a respective operational amplifier 82 and 86. Specifically, the photodiode 60 is coupled to the inverting input terminal of the operational amplifier 82 having coupled between an output thereof and the inverting input terminal thereof a 1M ohm resistor 84. Similarly, the photodiode 62 is coupled to the inverting input terminal of the operational amplifier 86, the output of which is coupled back to the inverting input terminal via a 1M ohm resistor 88. Because the photodetectors 60 and 62 are operated in a photoconductive mode, the optical sensor 38 has improved sensitivity and a faster switching speed. The outputs of the respective operational amplifiers 82 and 86 are amplified by the respective operational amplifiers 90 and 92. The outputs of the amplifiers 90 and 92 are coupled to a variable resistor 94 which is adjustable so as to balance the outputs from the photodiodes 60 and 62. Thus, the circuit can compensate for a light source that is not exactly centered between the photodetection elements 60 and 62. The output of the amplifier 90 representing the amount of light impinging on the photodetector element 60 is applied to an inverting input terminal of a differential amplifier 98 whereas the output of the amplifier 92 representing the amount of light impinging on the other photodetector element 62 is applied to the non-inverting input terminal of the differential amplifier 98. The differential amplifier 98 is responsive to the signals applied to its inverting and non-inverting input terminals to produce a difference signal at the output thereof representing the difference in the amount of light impinging on the respective photodetector elements 60 and 62. As discussed above, the output from the differential amplifier 98 may be compared to a first reference signal to detect a leading edge of the crack or fissure 29' and to a second reference signal to detect a trailing edge of the crack or fissure 29'. These leading and trailing edge indicative signals can thereafter be used to control the registration of a label with respect to a printhead so that printed information can be accurately positioned on the label or other record member.

It is noted, that the optical detector arrangement illustrated in FIGS. 18–20 is also suitable for detecting an indicium such as a black mark carried on the label web, as opposed to a crack or fissure 29'. Because the difference circuit detects the difference in the amount of light impinging on the respective active areas 60 and 62, it is capable of detecting the leading and trailing edges of a black mark wherein the black mark absorbs the light so as to cause a substantial drop in the amount of light detected when the black mark is above an active portion of the optical detector 38 as opposed to the lighter areas of the composite label web which allows some light to pass therethrough and be detected. Thus, the same circuitry can be employed to detect indicia in the forms of cracks or fissures 29' and black marks.

Other embodiments or modifications of the invention will suggest themselves to those skilled in the art, and all such of these as come within the spirit of this invention are included within its scope as best defined by the appended claims.

I claim:

1. An optical detection system for a printer having a printhead for printing on a web of record members, said web of record members having indicia with a predetermined relationship with the record members spaced along the length of the web with each indicium having a leading and trailing edge comprising:

a source of light;

an optical detector positioned relative to said source of light to detect light impinging on said detector and said detector being spaced from said source of light to allow said web of record members to pass therebetween, said detector generating a first output signal representing an amount of light impinging on a first portion of said detector and generating a second output signal representing an amount of light impinging on a second portion of said detector;

a circuit responsive to said first output signal and to said second output signal for producing a difference signal representative of the difference between said first and second output signals, said difference signal being indicative of the presence or absence of said indicium; and an edge detector responsive to said difference signal for detecting at least one edge of said indicium for registration of a record member with said printhead.

2. A system for detecting indicia on a web of record members as recited in claim 1, wherein said source of light is a source of infrared light.

3. A system for detecting indicia on a web of record members as recited in claim 1, wherein said optical detector is operated in a photoconductive mode of operation.

4. A system for detecting indicia on a web of record members as recited in claim 1, wherein said edge detector includes means for comparing said difference signal to a reference signal to identify an edge of said indicium.

5. An optical detection system for a printer having a printhead for printing on a web of record members, said web of record members having indicia with a predetermined relationship with the record members spaced along the length of the web with each indicium having a leading and trailing edge comprising:

a source of light positioned relative to a first side of said web of record members;

a first photodetector element for generating a first output signal representing an amount of light impinging on said first element;

a second photodetector element spaced a predetermined distance from said first element for generating a second output signal representing an amount of light impinging on said second element, said first and second photodetector elements being positioned on a second side of web of record members opposite to said first side and said source of light so as to detect light from said source as said indicium in said web of record members passes between said source of light and said first and second photodetector elements; and a circuit responsive to said first output signal and to said second output signal for producing a difference signal representative of the difference between said first and second output signals, said difference signal being indicative of the presence or absence of said indicium; and an edge detector responsive to said difference signal for detecting at least one edge of said indicium for registration of a record member with said printhead.

6. A system for detecting indicia on a web of record members as recited in claim 5, wherein said source of light is a source of infrared light.

7. A system for detecting indicia on a web of record members as recited in claim 5, wherein each of said first and said second photodetector elements is operated in a photoconductive mode of operation.

8. A system for detecting indicia on a web of record members as recited in claim 5, wherein said edge detector includes means for comparing said difference signal to a reference signal to identify an edge of said indicia.

9. An optical detection system for a printer having a printhead for printing on a web of record members, said web of record members having indicia spaced alone the length of the web and each indicium having a leading and trailing edge comprising:

a source of light;

an optical detector positioned relative to said source of light to detect light impinging on said detector and said detector being spaced from said source of light to allow said web of record members with said indicia to pass therebetween, said detector generating a first output signal representing an amount of light impinging on a first portion of said detector and generating a second output signal representing an amount of light impinging on a second portion of said detector;

a difference circuit responsive to said first output signal and to said second output signal for producing a difference signal representing the difference between said first and second output signals; and an edge detector including a first comparator for comparing said difference signal to a first reference signal to provide a first edge signal representing the detection of one of said edges of said indicium if said difference signal is above said first reference signal and a second comparator for comparing said difference signal to a second reference signal to provide a second edge signal representing the detection of another of said edges of said indicium if said difference signal is below said second reference signal.

10. A system for detecting indicia on a web of record members as recited in claim 9, wherein each indicium is an optically detectable crack or fissure.

11. A system for detecting indicium as recited in claim 1 wherein said indicium is a mark.

12. A system for detecting indicium as recited in claim 1 wherein said indicium is a crack or fissure.

13. A system for detecting indicium as recited in claim 1 wherein said indicium allows more light to impinge upon said optical detector than a record member.

14. An optical detection system for a printer having a printhead for printing on a web of record members said web of record members having areas of opacity different than the opacity of said record members, said areas having a predetermined relationship with said record members so as to be usable for registration and each of said areas having a leading edge and a trailing edge, said optical detection system comprising:

a source of light;

an optical detector positioned relative to said source of light to detect light impinging on said detector and said detector being spaced from said source of light to allow said record members to pass therebetween, said detector generating a first output signal representing an amount of light impinging on a first portion of said detector and generating a second output signal representing an amount of light impinging on a second portion of said detector; and a circuit responsive to said first and second detector output signals for generating a leading edge signal representing a leading edge of one of said areas of opacity different from said record members and a trailing edge signal representing a trailing edge of one of said areas for the registration of a record member with said printhead.

15. An optical detection system for a printer as recited in claim 14 wherein said area of opacity different from said record members is a black mark.

16. An optical detection system for a printer as recited in claim 14 wherein said area of opacity different from said record members allows more light to impinge on said optical detector than said record members.

17. An optical detection system for a printer as recited in claim 14 wherein said circuit includes a first circuit portion responsive to said first and second output signals of the detector to provide a difference signal representing the difference between the first and second output signals and a second circuit portion for comparing said difference signal to a first reference signal and a second reference signal to generate said leading edge signal and trailing edge signal respectively.

18. An optical detection system for a printer having a printhead for printing on a web of record members said web of record members having areas of opacity different than the opacity of said record members, said areas having a predetermined relationship with said record members and each of said areas having a leading edge and a trailing edge, said optical detection system comprising:

a source of light;

an optical detector positioned relative to said source of light to detect an amount of light impinging on said detector and to provide one or more signals representative of the amount of light impinging thereon;

an edge detector responsive to said one or more signals from said optical detector for detecting a leading edge of an area of opacity different than the opacity of a record member and for detecting a trailing edge of an area of opacity different than the opacity of a record member, said edge detector providing a leading edge signal and a trailing edge signal representative of the respective detected leading and trailing edges for the registration of record members with said printhead.

19. An optical detection system for a printer as recited in claim 18 wherein said area of opacity different from said record members is a mark.

20. An optical detection system for a printer as recited in claim 18 wherein said area of opacity different from said record members allows more light to impinge on said optical detector than said record members.

* * * * *

UNITED STATES PATENT AND TRADEMARK OFFICE
CERTIFICATE OF CORRECTION

PATENT NO.   : 5,760,414
DATED        : June 2, 1998
INVENTOR(S)  : John W. Taylor It is certified that error appears in the above-indentified patent and that said Letters Patent is hereby corrected as shown below:

Column 8, claim 9, line 31 "alone" should be --along--.

Signed and Sealed this

Tenth Day of November 1998

Attest:

BRUCE LEHMAN

Attesting Officer

Commissioner of Patents and Trademarks